(12) United States Patent
Tomita et al.

(10) Patent No.: US 8,137,353 B2
(45) Date of Patent: Mar. 20, 2012

(54) SURGICAL SAW

(75) Inventors: Katsuro Tomita, Ishikawa (JP); Shigeo Kawakami, Tochigi (JP); Masaaki Matsutani, Tochigi (JP); Kanji Matsutani, Tochigi (JP)

(73) Assignee: MANI., Inc., Tochigi (JP)

( * ) Notice: Subject to any disclaimer, the term of this patent is extended or adjusted under 35 U.S.C. 154(b) by 658 days.

(21) Appl. No.: 11/430,823

(22) Filed: May 10, 2006

(65) Prior Publication Data

US 2007/0055262 A1 Mar. 8, 2007

(30) Foreign Application Priority Data

May 10, 2005 (JP) ................................. 2005-137155

(51) Int. Cl.
*A61B 17/00* (2006.01)
(52) U.S. Cl. ........................................................ 606/82
(58) Field of Classification Search ....................... 606/82
See application file for complete search history.

(56) References Cited

U.S. PATENT DOCUMENTS

| | | | | | |
|---|---|---|---|---|---|
| 184,804 | A | * | 11/1876 | Selby | 606/176 |
| 1,306,636 | A | * | 6/1919 | Stohlmann | 57/211 |
| 2,752,964 | A | * | 7/1956 | Prusinski | 30/166.3 |
| 3,150,470 | A | * | 9/1964 | Barron | 451/532 |
| 4,258,763 | A | * | 3/1981 | Figueredo et al. | 144/34.1 |
| 4,464,836 | A | * | 8/1984 | Hissa | 30/92 |
| 4,709,699 | A | * | 12/1987 | Michael et al. | 606/177 |
| 5,817,711 | A | * | 10/1998 | Kambe et al. | 524/501 |
| 6,063,083 | A | * | 5/2000 | Duong-Van | 606/45 |
| 6,152,894 | A | * | 11/2000 | Kubler | 604/22 |
| 2002/0151905 | A1 | * | 10/2002 | Ishihara et al. | 606/108 |
| 2003/0224705 | A1 | * | 12/2003 | Schmidt | 451/278 |
| 2005/0216023 | A1 | * | 9/2005 | Aram et al. | 606/86 |
| 2006/0089609 | A1 | * | 4/2006 | Bleich et al. | 604/272 |
| 2008/0255624 | A1 | * | 10/2008 | Arcenio et al. | 606/86 R |

FOREIGN PATENT DOCUMENTS

JP 3018201 U 11/1995

OTHER PUBLICATIONS

K. Tomita et al., The Threadwire Saw: a New Device for Cutting Bone. A Brief Note, Dec. 1996, JBJS, vol. 78-A, No. 12, pp. 1915-1917.*
Fred H. Albee, Bone Surgery with Machine Tools, Apr. 1936, The Scientific American Digest, pp. 178-181.*

* cited by examiner

*Primary Examiner* — Nicholas Woodall
(74) *Attorney, Agent, or Firm* — Orion Consulting, Ltd.; Joseph P. Farrar

(57) ABSTRACT

A surgical saw for cutting bone that can be used with ease in tight places yet maintain sufficient cutting power. The surgical saw 10 has a flexible linear body made of twisted stainless steel wire and cutting parts formed on the flexible linear body. The cutting parts are made of abrasive material affixed to the flexible linear body 12a alternating with portions of the flexible linear body with no abrasive particles 12b. Auxiliary cutting parts 13 of lesser cutting power may be provided along both lateral sides of each of the cutting parts 12.

5 Claims, 4 Drawing Sheets

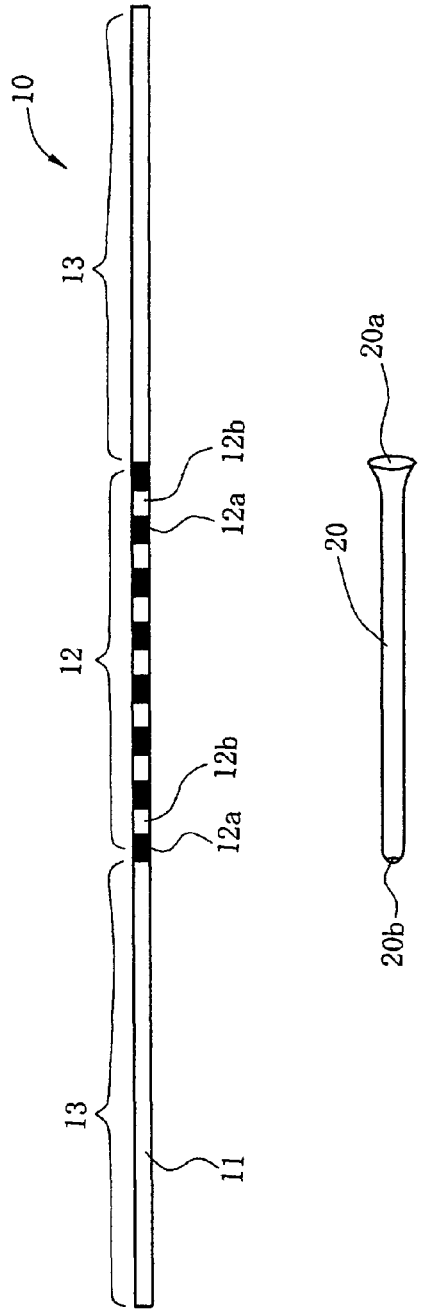
Fig. 1A
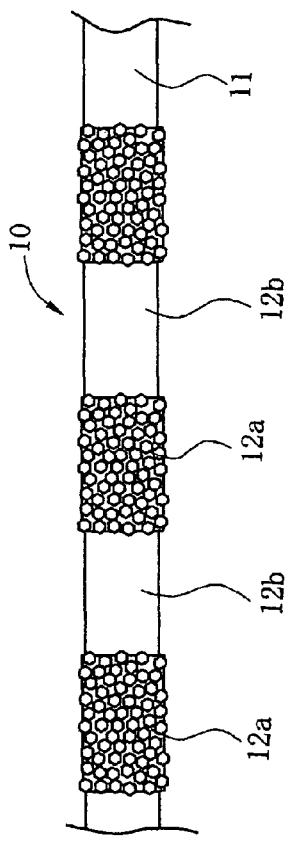
Fig. 1B
Fig. 1C

SURGICAL SAW

BACKGROUND OF THE INVENTION

1. Field of the Invention

The present invention relates to a surgical saw, and more particularly, to a surgical saw suitable for cutting bones such as the spine, the skull and so forth.

2. Background of the Invention

In some surgical operations, parts of bones are removed or bones are completely cut, and at such times a special saw for bones is used. As the conventional saw used for this purpose, a thin blade-shaped saw blade is used. However, a blade-shaped saw cannot be used in tight places, and moreover, tissue such as the spinal cord and the dura mater near the bone that is cut into or completely severed is easily damaged in such operations. Nerves (such as the spinal cord) pass through the dura mater, and particularly since the dura mater is thin and soft it is easily damaged. If the dura mater is damaged, the nerves can also be damaged, leading to such serious conditions as hemiplegia. Accordingly, it is absolutely vital to avoid damaging the dura mater.

Consequently, Japanese Registered Utility Model No. 3018201 proposes a surgical saw having a forked frame with two arms is proposed, with a wire strung between the tips of the two arms of the frame and the base of the frame attached to a vibrating device such as a reciprocator.

A stranded wire made of a metal such as stainless steel is used for the wire of the surgical saw described in Japanese Registered Utility Model No. 3018201, with the wire given a coarse surface. The coarseness of the surface cuts the bone.

However, the saw described in Japanese Registered Utility Model No. 3018201, because it coarsens the surface of metal wire, suffers from inadequate cutting power. In addition, the wire is strung straight between the tips of the arms, which necessitates a working space at least equal to the length of the wire and thus makes the saw difficult to use in tight places.

SUMMARY OF THE INVENTION

Accordingly, the present invention is conceived as a solution to the above-described problems of the conventional art, and has as its object to provide a surgical saw that can be used easily in tight places and has adequate cutting power.

To achieve the above-described object, according to a first aspect of the present invention there is provided a surgical saw comprising a flexible linear body, one or more than two cutting parts adapted to cut hard tissue such as bone, each one cutting part is comprised of two parts alternatively provided on the flexible linear body, one is a part wherein abrasive particles are affixed to the flexible linear body and another is a part wherein no abrasive particles are affixed to the flexible linear body.

In addition, according to a second aspect of the present invention there is provided a surgical saw comprising a flexible linear body, cutting parts adapted to cut hard tissue such as bone affixed to portions of the flexible linear body, and auxiliary cutting parts with lesser cutting power than the cutting parts affixed to other portions of the flexible linear body.

In addition, according to a third aspect of the present invention there is provided a surgical saw comprising a flexible linear body and cutting parts adapted to cut hard tissue such as bone affixed to portions of the flexible linear body, wherein at least the cutting parts of the flexible linear body are coated with a lubricating material.

The above-described linear body may be a single wire of stainless steel or a stranded wire.

A surgical saw according to a first aspect of the present invention can maintain flexibility by alternating portions where abrasive particles are affixed for cutting with portions with no abrasive particles affixed, and therefore can be used in tight places. Moreover, cutting power sufficient to cut through such hard tissue as bone can be obtained with the surgical saw of the present invention. In addition, according to a second aspect of the present invention, auxiliary cutting parts are provided in addition to the cutting part to enable bone to be cut without damaging soft tissue such as blood vessels and nerves (including thick nerves such as the spinal cord). In addition, according to a third aspect of the present invention, the surgical saw is coated with a lubricating material and can therefore prevent leakage of toxic material from the linear body, thereby improving the suitability of the surgical saw for work with living tissue. Additionally, the lubricating coating enables the surgical saw to cut smoothly.

Other features, objects and advantages of the present invention will be apparent from the following description when taken in conjunction with the accompanying drawings, in which like reference characters designate the same or similar parts throughout the figures thereof.

BRIEF DESCRIPTION OF THE DRAWINGS

FIGS. 1A, 1B and 1C and FIG. 2 showing a surgical saw according to one embodiment of the present invention, in which FIG. 1A shows an overall view, FIG. 1B shows a guide tube, and FIG. 1C shows an enlarged view of a portion of the cutting part of the surgical saw;

FIG. 2 is a perspective view of the surgical saw of the present invention used to open the spine;

DETAILED DESCRIPTION OF THE PREFERRED EMBODIMENTS

Figure 2:
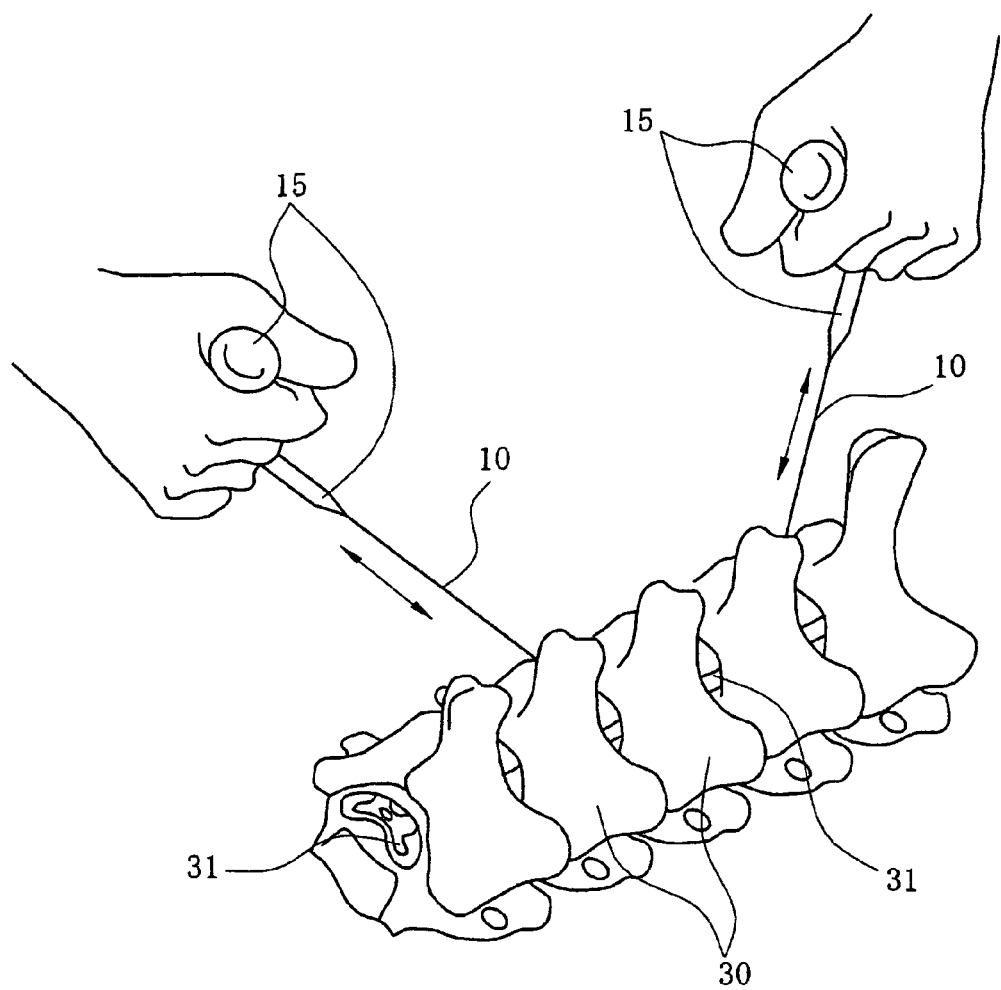

Preferred embodiments of the present invention will now be described in detail, with reference to the accompanying drawings.

FIGS. 1A, 1B and 1C show a surgical saw according to one embodiment of the present invention, in which FIG. 1A shows an overall view, FIG. 1B shows a guide tube, and FIG. 1C shows an enlarged view of a portion of the cutting part of the surgical saw.

The surgical saw 10 of the present invention is composed of a linear body 11, a cutting part 12 formed on an intermediate portion of a linear body 11 and auxiliary cutting parts 13, 13 disposed on both lateral sides of each of the cutting part 12.

The linear body 11 uses a stainless steel wire having a diameter of approximately 0.3-1.0 mm. Using stainless steel prevents rust, enabling the adverse effects of rust on human tissue to be eliminated. It is preferable to use something flexible that can bend to the shape of the bone for the linear body 11 although a single strand may be used provided that it is annealed, it is preferable to use a stranded wire or mesh line. Using stranded wire and mesh line makes it possible to obtain a linear body 11 that is flexible as well as strong. In addition, the surfaces of the stranded wire or mesh line are uneven, and this unevenness, although it provides little cutting power, nevertheless has enough cutting power to saw through bone without damaging soft tissue such as blood vessels and nerves. There is no particular limit on the number of strands in the stranded wire. In the present embodiment, the number of strands is 7×7 (for a total of 49 strands).

Although in the embodiment shown in the FIGS. 1A, 1B and 1C stainless steel stranded wire is used for the linear body 11 alternatively thread made of natural fiber or synthetic fiber may be used. In the latter case, spun yarn or a single filament or spun multiple filaments may be used.

As shown in FIG. 1C, the a cutting part 12 is composed of alternating portions 12a where abrasive particles are affixed to the linear body 11 and portions 12b where no abrasive particles are affixed to the linear body 11.

Although there are no particular limitations on what may be used for the abrasive particles, it is preferable to use a hard substance such as diamond or cubic boron nitride (CBN) abrasive particles. In the present embodiment, diamond particles having a diameter of 30-40 μm are used. The abrasive particles may be affixed to the linear body 11 with an adhesive agent. However, such adhesive agent should be one that is not harmful to humans. In addition, because the abrasive particles come off during cutting of bone, it is preferable to use a strong adhesive in order to minimize such loss. In the present embodiment, the diamond particles are affixed to the surface of the stainless steel linear body 11 using a nickel welding commonly used in medical instruments.

The portion 12a wherein the abrasive particles are affixed becomes rigid and loses flexibility, and therefore portions where no abrasive particles are provided so as to maintain flexibility. Although it is not necessary that the portions 12a of the linear body 11 where there are abrasive particles and the portions 12b of the linear body 11 where there are no abrasive particles be spaced equidistantly apart, doing so stabilizes the cutting power of the surgical saw 10. The lengths of the two portions need not be identical, and thus may be different. In the present embodiment, both portions are 2 mm long, although the length can vary in a range of 1-5 mm. If the length of the portion is less than 1 mm, the abrasive particles tend not to be sufficiently affixed. If the length is greater than 5 mm, the surgical saw tends to lose flexibility.

Auxiliary cutting parts 13 are formed along both lateral sides of each cutting parts 12. These auxiliary cutting parts 13 are portions of the linear body 11 that are not shaped or machined in any way. The linear body 11 is made of material that is harder than bone, and furthermore, is stranded wire or mesh line having a coarse surface. Therefore, although its cutting power is not as great as that of the cutting part 12, the linear body 11 itself, by reciprocal strokes, can cut bone.

The surgical saw 10 is coated with a lubricating material. Silicon resin and TEFLON (TEFLON® is a registered trademark of E. I. DU PONT DE NEMOURS AND COMPANY, a Delaware corporation) may be used as lubricants. The coating prevents the linear body 11 from directly contacting tissue and can prevent leakage of toxic materials such as nickel and the like from the linear body 11 and thus improves the suitability of the saw for use with living tissue. In addition, where the abrasive particles affixed to the linear body 11 are large and apt to cut too much and in an unstable manner, use of the coating allows the surgical saw 10 to cut smoothly. Although the coating may be applied only to the cutting part 12, it is preferable that the auxiliary cutting parts 13 be coated as well. Provided that it provides good lubrication, the substances that may be used as the lubricant are not limited, and moreover are not limited to fluids and may be powders.

FIG. 1B shows a guide tube 20. The guide tube 20 is a flexible hollow tube made of synthetic resin having a flared entry end 20a and an exit end 20b through which the surgical saw can pass.

One end of the surgical saw is inserted into a gap between the bone to be cut and the adjacent living tissue, pulled from the opposite side of the bone and the ends of the surgical saw 10 alternately pulled to cut. However, the gap between the bone and the adjacent living tissue is small, and consequently there is a risk of damaging the tissue if the surgical saw 10 were to be passed directly through the gap. Therefore, by first passing the guide tube 20 through the gap and then passing the surgical saw 10 through the guide tube 20, damage to the tissue can be avoided and the surgical saw 10 passed safely from one side of the bone to the opposite side.

FIG. 2 is a perspective view of the cutting open of spinal vertebrae 30 with the surgical saw 10 of the present invention. The auxiliary cutting parts 13 may be grasped by hand so as to allow the ends of the surgical saw 10 to be pulled alternately, although usually handles 15 are attached to the ends of the surgical saw 10. The bone(s) to be cut may be a single vertebra 30 or the surgical saw 10 may straddle multiple vertebrae 30 as shown in FIG. 2 allowing multiple vertebrae to be cut simultaneously.

The spinal cord 31 sheathed in a dura mater passes through the interior of the spinal vertebrae 30, and it is necessary to avoid damaging the spinal cord when cutting. Accordingly, FIGS. 3A, 3B, 3C, 3D, and 3E illustrate the use of the surgical saw 10 of the present invention.

The diagrams show schematically the spinal vertebrae 30. The spinal vertebrae 30 are substantially annular in shape, although to facilitate the description a portion thereof is cut away from the drawing. As described above, the spinal cord 31 is the living tissue that passes through the spinal vertebrae 30.

Figure 3:
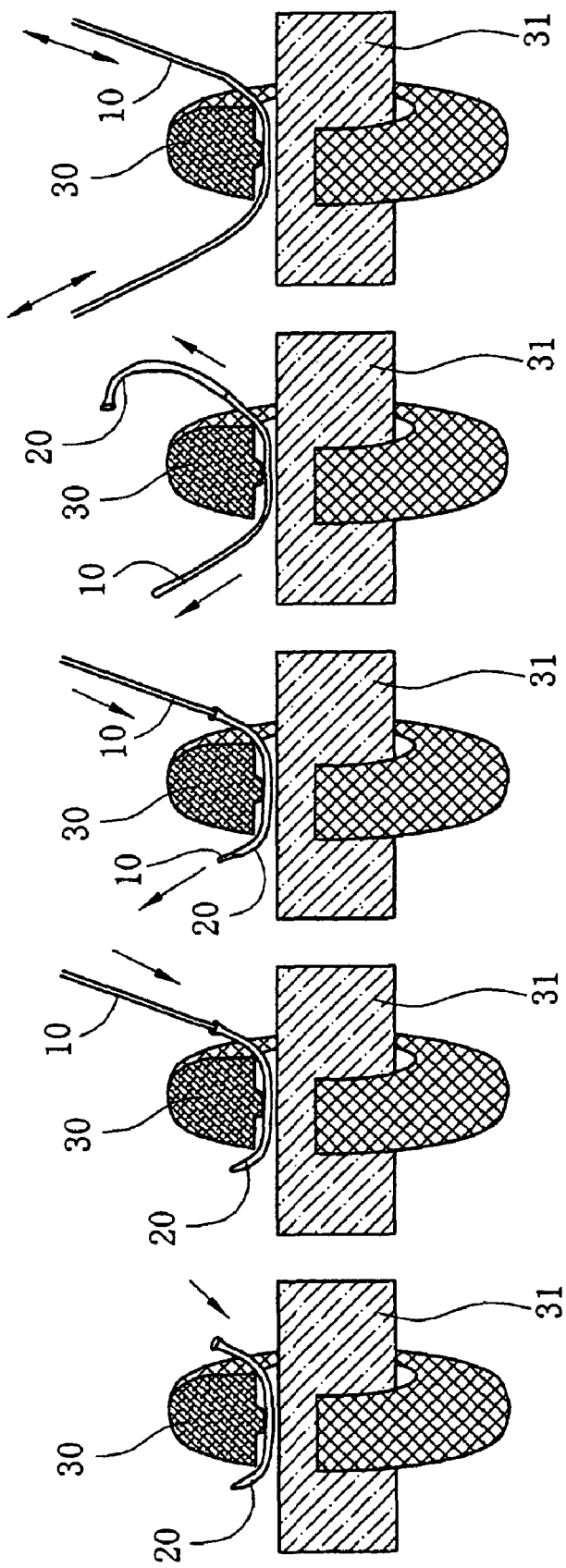
FIGS. 3A, 3B, 3C, 3D and 3E illustrate steps in the method of using the surgical saw of the present invention.

Prior to inserting the surgical saw 10 inside the spinal vertebrae 30, first, as shown in FIG. 3A, the exit end 20b (that is, the leading end) of the guide tube 20 is inserted from one side of the spinal vertebra 30 to be treated in the direction indicated by the arrow and the leading end of the guide tube 20 is projected out the opposite side of the spinal vertebra 30.

Next, as shown in FIG. 3B, one end of the surgical saw 10 is inserted into the guide tube 20 from the entry end 20a. The surgical saw 10 passes through the hollow interior of the guide tube 20 toward the leading end.

When the tip of the surgical saw 10 protrudes from the exit end 20b of the guide tube 20 as shown in FIG. 3C, it is grasped with forceps and pulled. When the surgical saw 10 is pulled through, the guide tube 20 is pulled out and removed as shown in FIG. 3D.

The entry end 20a of the guide tube 20 is flared as shown in FIG. 1B, and for that reason, when the guide tube 20 is inserted and removed it is preferable that it be done so that this portion does not pass between the spinal vertebrae 30 and the spinal cord 31, thereby enabling damage to the spinal cord 31 to be prevented.

Then, as shown in FIG. 3E, the ends of the surgical saw 10 are pulled alternately so as to cut. Where there is soft tissue such as blood vessels and nerves nearby as is the case with the spinal vertebrae 30, it is preferable that initially the spinal vertebrae 30 be cut into slightly with the auxiliary cutting parts 13 so as to provide a groove for the cutting parts 12 of the surgical saw 10 to follow, after which the spinal vertebrae 30 may be cut away with the cutting parts 12. The cutting force of the auxiliary cutting parts 13 is small, and therefore the blood vessels and nerves can be pushed aside and moved away from the location of the cut without damaging them.

Then, if bone is to be cut with the cutting parts 12, these cutting parts 12 pass through a space formed (cut away) by the auxiliary cutting parts 13, and therefore damage to the blood vessels and nerves can be prevented.

It should be noted that although in the method shown in FIGS. 3A-3E the guide tube 20 is inserted into the target surgical area first and then the surgical saw 10 is inserted into the guide tube 20, alternatively the surgical saw 10 can be inserted in the guide tube 20 first and then the guide tube 20 inserted into the surgical area.

Cutting Test

A cutting test was conducted of the surgical saw of the present invention and a surgical saw composed of stainless steel stranded wire. The sample used for cutting was an epoxy resin rod whose consistency resembles bone having a diameter of 12 mm, and a comparison made of the number of strokes each saw took to cut through the rod.

The surgical saw 10 of the present invention consisted of a cutting part 12 having a length of 200 mm and two auxiliary cutting parts 13 each having a length of 300 mm, for a total length of 800 mm. The surgical saw 10 used diamond abrasive particles of a particle size of 30-40 μm, with lengths of affixed abrasive particles and lengths with no abrasive particles each provided at a pitch of 2 mm. The overall length of the surgical saw composed of stainless steel stranded wire with no abrasive particles affixed thereto was 800 mm. The stranded wire is the same in both saws. In addition, 800 g plumbs similar to weight during actual use were attached to both ends of each saw and the saws moved reciprocally. The surgical saw of the present invention took approximately 400 strokes to cut through the rod, whereas the comparative example without abrasive particles could not cut through the rod even after 3,000 strokes.

Figure 4:
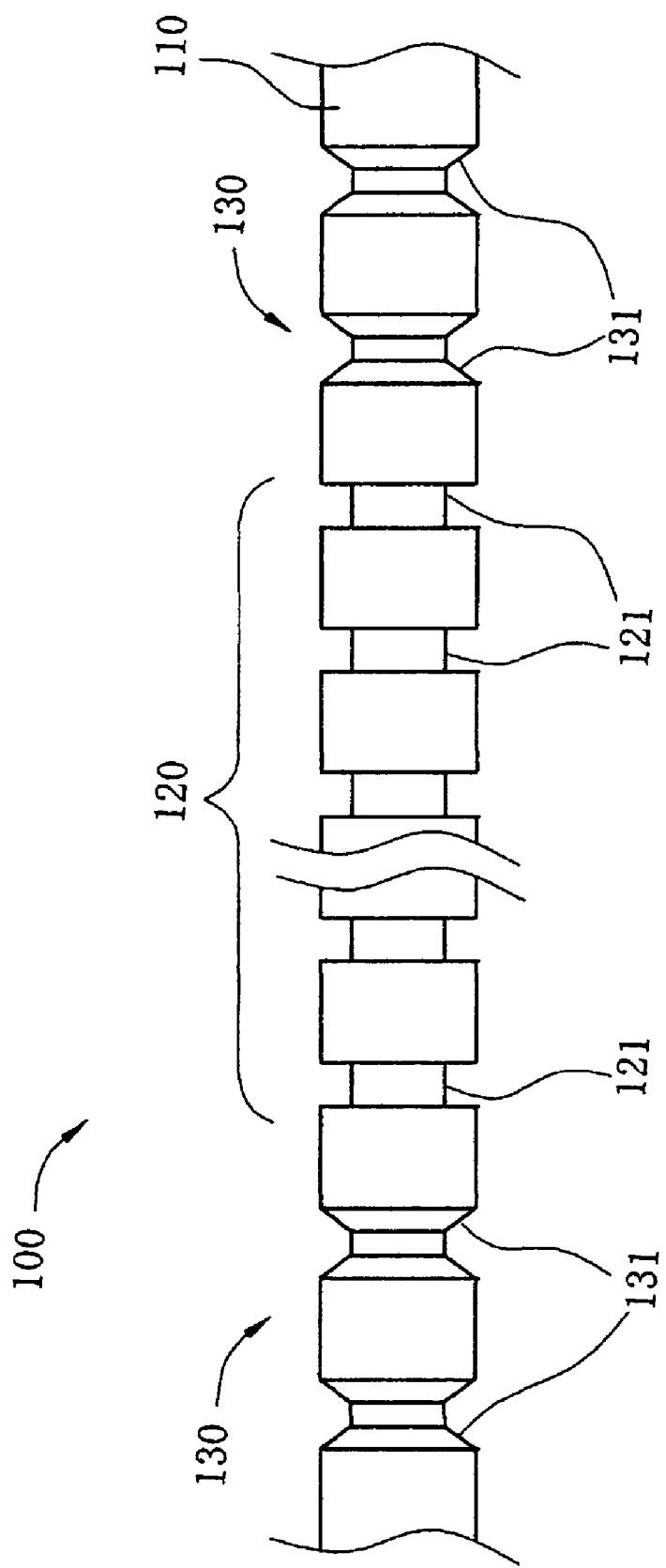
FIG. 4 is an enlarged view of the main part of a second embodiment of a surgical saw according to the present invention.

It should be noted that although the present invention is described in terms of an example in which abrasive particles are affixed to the linear body 11, the present invention is not limited thereto. Thus, for example, as shown in FIG. 4, the shape of the linear body may be machined so as to form the cutting parts. With the surgical saw 100 of this example, a cutting part 120 provided with multiple grooves 121 equidistantly spaced is formed at an intermediate portion of the linear body 110, at both ends of which auxiliary cutting parts 130 forming gently angled grooves 131 are formed. The grooves in the cutting parts 120 are cut at right angles and therefore cut well, whereas the grooves of the auxiliary cutting parts 130 are gently angled and therefore do not cut very well, thereby enabling bone to be cut without damaging adjacent blood vessels and nerves.

As many apparently widely different embodiments of the present invention can be made without departing from the spirit and scope thereof, it is to be understood that the invention is not limited to the specific preferred embodiments described above thereof except as defined in the claims.

What is claimed is:

1. A surgical saw comprising:
   a flexible linear body;
   a primary cutting part adapted to cut hard tissue such as bone affixed to a portion of the flexible linear body, the primary cutting part including portions where abrasive particles are attached to the flexible linear body alternating with portions where no abrasive particles are attached to the flexible linear body, the portions with abrasive particles having a length of 1-5 mm;
   secondary cutting parts each having a length longer than a length of the primary cutting part, adapted to cut hard tissue such as bone, having a coarse surface where no abrasive particles are attached to the flexible linear body, provided on both ends of the primary cutting part; and
   a flexible hollow tube of synthetic resin, dimensioned to allow the flexible linear body to pass therethrough.

2. The surgical saw according to claim 1, wherein the flexible linear body is a single strand of metal wire,
   a plurality of spaced grooves is provided on the flexible linear body in the direction of the width of the flexible linear body so as to form the cutting parts therebetween,
   a plurality of spaced grooves is provided on both ends of the flexible linear body in the direction of the width of the flexible linear body so as to form the auxiliary cutting parts therebetween, the grooves gently angled along both lateral sides of each such auxiliary cutting part,
   the auxiliary cutting parts formed on both ends of the cutting part, at both ends of the flexible linear body.

3. The surgical saw according to claim 1, wherein the flexible linear body is stranded wire or mesh line.

4. The surgical saw according to claim 1, wherein at least the primary cutting part of the flexible linear body is coated with a lubricating material.

5. The surgical saw according to claim 1, further comprising a pair of handles attached at opposed ends of the flexible linear body.

\* \* \* \* \*